United States Patent
DelMonte et al.

(10) Patent No.: US 9,556,204 B2
(45) Date of Patent: Jan. 31, 2017

(54) METHODS AND INTERMEDIATES FOR THE PREPARATION OF (4BS,5AR)-12-CYCLOHEXYL-N-(N,N-DIMETHYLSULFAMOYL)-3-METHOXY-5A-((1R,5S)-3-METHYL-3,8-DIAZABICYCLO [3.2.1]OCTANE-8-CARBONYL)-4B,5,5A,6-TETRAHYDROBENZO [3,4]CYCLOPROPA[5,6]AZEPINO[1,2-A] INDOLE-9-CARBOXAMIDE

(71) Applicant: BRISTOL-MYERS SQUIBB COMPANY, Princeton, NJ (US)

(72) Inventors: Albert J. DelMonte, Belle Mead, NJ (US); Kenneth J. Natalie, Jr., Flemington, NJ (US); Kenneth J. Fraunhoffer, Princeton, NJ (US); Christina Ann Risatti, Clarksburg, NJ (US); Chao Hang, Monmouth Junction, NJ (US); Zhinong Gao, Princeton, NJ (US); Akin H. Davulcu, Yardley, PA (US); Wenhao Hu, Shanghai (CN)

(73) Assignee: Bristol-Myers Squibb Company, Princeton, NJ (US)

( * ) Notice: Subject to any disclaimer, the term of this patent is extended or adjusted under 35 U.S.C. 154(b) by 40 days.

(21) Appl. No.: 14/414,475

(22) PCT Filed: Jul. 16, 2013

(86) PCT No.: PCT/US2013/050640
§ 371 (c)(1),
(2) Date: Jan. 13, 2015

(87) PCT Pub. No.: WO2014/014885
PCT Pub. Date: Jan. 23, 2014

(65) Prior Publication Data
US 2015/0133654 A1    May 14, 2015

Related U.S. Application Data

(60) Provisional application No. 61/672,905, filed on Jul. 18, 2012.

(51) Int. Cl.
| | | |
|---|---|---|
| C07C 62/10 | (2006.01) |
| C07C 69/734 | (2006.01) |
| C07C 69/757 | (2006.01) |
| C07D 209/08 | (2006.01) |
| C07D 487/04 | (2006.01) |
| C07D 519/00 | (2006.01) |
| C07C 211/45 | (2006.01) |
| C07C 233/05 | (2006.01) |

(52) U.S. Cl.
CPC ............ *C07D 519/00* (2013.01); *C07C 62/10* (2013.01); *C07C 69/734* (2013.01); *C07C 69/757* (2013.01); *C07C 211/45* (2013.01); *C07C 233/05* (2013.01); *C07D 209/08* (2013.01); *C07D 487/04* (2013.01)

(58) Field of Classification Search
CPC ...... C07C 62/10; C07C 69/734; C07C 69/757; C07D 209/08; C07D 487/04; C07D 519/00
USPC ....... 540/576; 548/503; 560/59, 61; 562/469
See application file for complete search history.

(56) References Cited

U.S. PATENT DOCUMENTS 7,456,166 B2    11/2008   Bender et al.

FOREIGN PATENT DOCUMENTS

WO    WO 89/02891 A1    4/1989

*Primary Examiner* — Brenda Coleman
(74) *Attorney, Agent, or Firm* — James Epperson

(57) ABSTRACT

The present invention provides methods and intermediates for the preparation of (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide (formula I), including pharmaceutically acceptable salts. The compound has activity against hepatitis C virus (HCV) and may be useful in treating those infected with HCV.

9 Claims, No Drawings

METHODS AND INTERMEDIATES FOR THE PREPARATION OF (4BS,5AR)-12-CYCLOHEXYL-N-(N,N-DIMETHYLSULFAMOYL)-3-METHOXY-5A-((1R,5S)-3-METHYL-3,8-DIAZABICYCLO[3.2.1]OCTANE-8-CARBONYL)-4B,5,5A,6-TETRAHYDROBENZO[3,4]CYCLOPROPA[5,6]AZEPINO[1,2-A]INDOLE-9-CARBOXAMIDE

BACKGROUND OF THE INVENTION

The disclosure relates to methods of preparing (4bS,5aR)-12-cyclohexyl-N—(N,N-dimethylsulfamoyl)-3-methoxy-5a-((1R,5S)-3-methyl-3,8-diazabicyclo[3.2.1]octane-8-carbonyl)-4b,5,5a,6-tetrahydrobenzo[3,4]cyclopropa[5,6]azepino[1,2-a]indole-9-carboxamide (Compound I, formula I), its salts, and intermediates in the preparation of this compound. The compound has activity against hepatitis C virus (HCV) and may be useful in treating those infected with HCV.

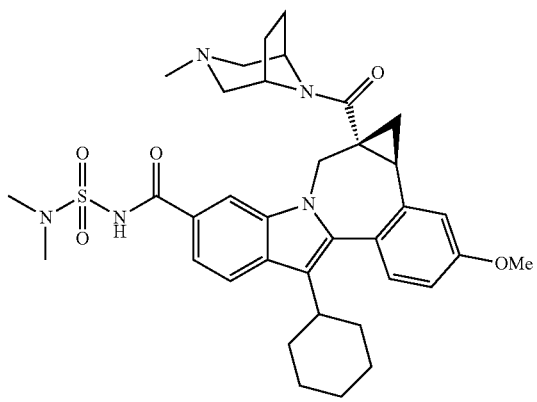

I

Hepatitis C virus (HCV) is a major human pathogen, infecting an estimated 170 million persons worldwide. Hepatitis C virus (HCV) is the most common bloodborne infection in the USA and worldwide and is the leading cause of liver transplantation (Eric Chak et. al. *Liver International* 2011, 1090-1101). A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

A number of compounds which are inhibitors of HCV NS5B are in clinical development or have advanced to clinical studies and been discontinued for various reasons. More specific to this application, HCV NS5B inhibitors which bind to a site referred to in the art as Site 1, including Compound I, have been disclosed in U.S. Pat. No. 7,456,166 (issued Nov. 25, 2008; US patent publication 20070270405, published Nov. 22, 2007).

For purposes of large-scale production there is a need for a high-yielding synthesis of compound of formula I and related analogs that is both efficient and cost-effective.

DESCRIPTION OF THE INVENTION

One aspect of the invention is a method for preparing the compound

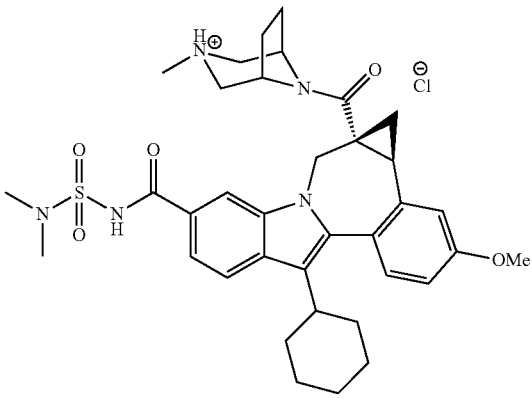

comprising amidation of the compound

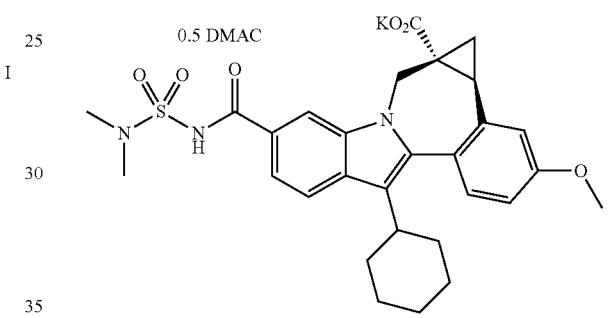

followed by crystallization.

Another aspect of this method further comprises the coupling of

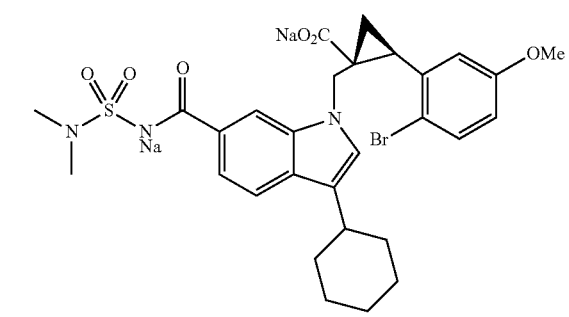

to generate the compound

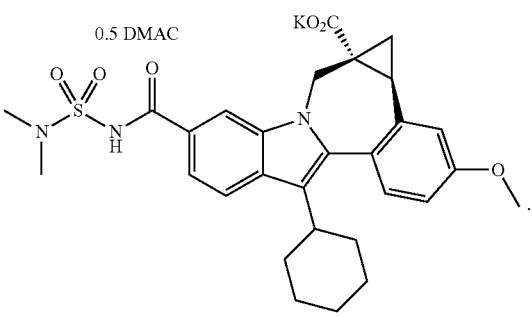

.

Another aspect of this method further comprises a method for the coupling of the compound

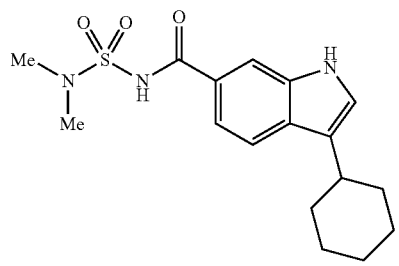 [SMILES: CN(C)S(=O)(=O)NC(=O)c1ccc2c(C3CCCCC3)c[nH]c2c1]

with the compound

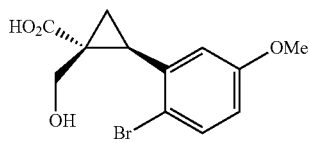 [SMILES: COc1ccc(Br)c([C@@H]2C[C@@]2(CO)C(=O)O)c1]

to generate the compound

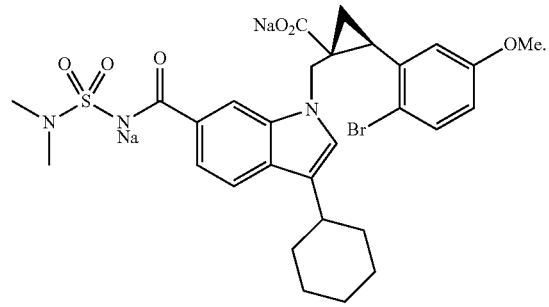

Another aspect of this method further comprises the reduction of the compound

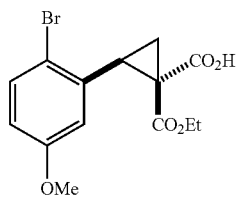

to generate the compound

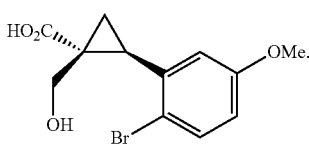 [SMILES: COc1ccc(Br)c([C@@H]2C[C@@]2(CO)C(=O)O)c1]

Another aspect of this method further comprises the cyclopropanation and hydrolysis of the compound

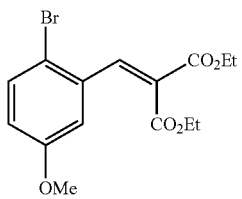

to generate the compound

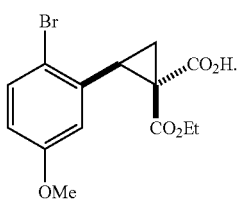

Another aspect of this invention is a method comprising the coupling of

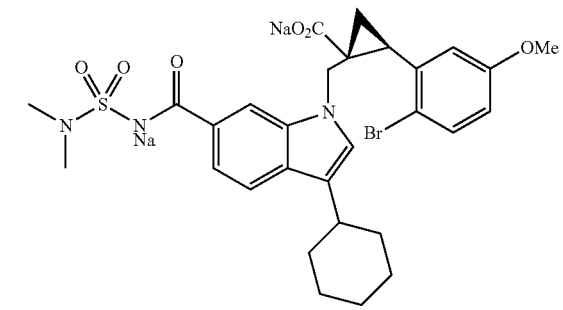

to generate the compound

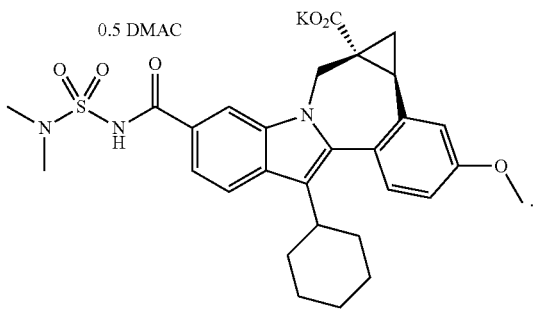

Another aspect of this invention is a method comprising the coupling of the compound

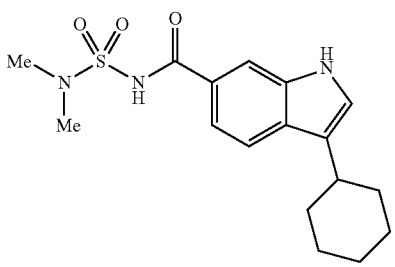 [SMILES: CN(C)S(=O)(=O)NC(=O)c1ccc2c(C3CCCCC3)c[nH]c2c1]

with the compound

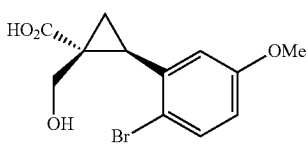 [SMILES: COc1ccc(Br)c([C@@H]2C[C@@]2(CO)C(=O)O)c1]

to generate the compound

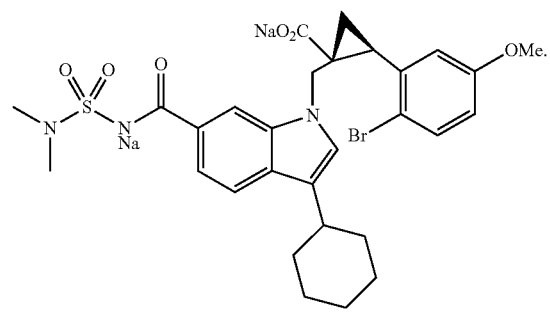

Another aspect of this invention is a method comprising the reduction of the compound

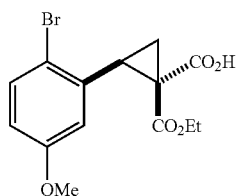

to generate the compound

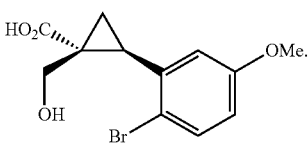 [SMILES: COc1ccc(Br)c([C@@H]2C[C@@]2(CO)C(=O)O)c1]

Another aspect of this invention is a method comprising the cyclopropanation and hydrolysis of the compound

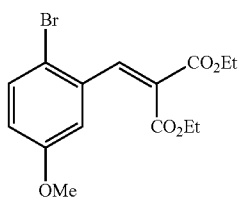 [SMILES: CCOC(=O)C(=Cc1cc(OC)ccc1Br)C(=O)OCC]

to generate the compound

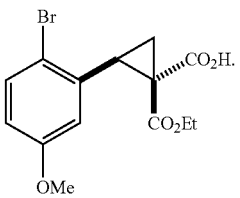

Another aspect of the invention is a method comprising the preparation of the compound

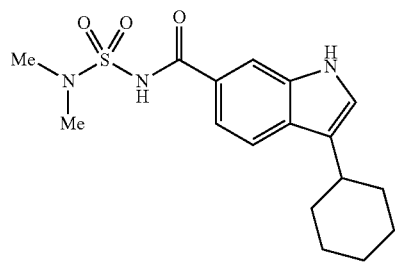 [SMILES: CN(C)S(=O)(=O)NC(=O)c1ccc2c(C3CCCCC3)c[nH]c2c1]

from indole-6-carboxylic acid by converting the acid moiety to the dimethylacylsulfonamide moiety followed by coupling to cyclohexanone and reduction.

Another aspect of the invention is a method comprising the preparation of the compound

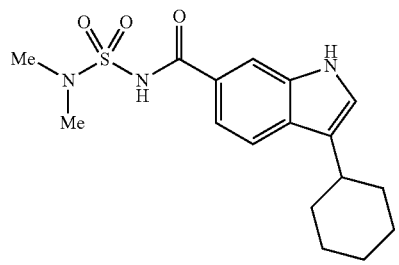 [SMILES: CN(C)S(=O)(=O)NC(=O)c1ccc2c(C3CCCCC3)c[nH]c2c1]

from 6-bromoindole by coupling and reduction with cyclohexanone followed by transitional metal catalyzed conversion to the dimethylacylsulfonamide with CO and dimethylsulfamide.

Another aspect of the invention is the compound

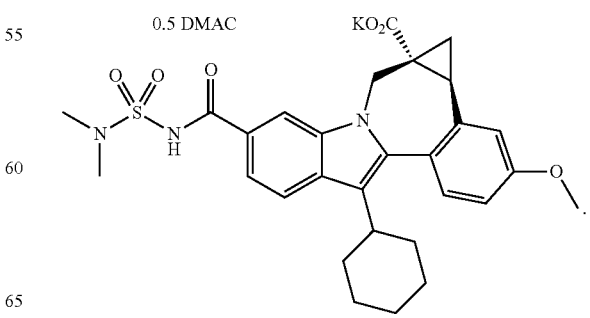

Another aspect of the invention is the compound

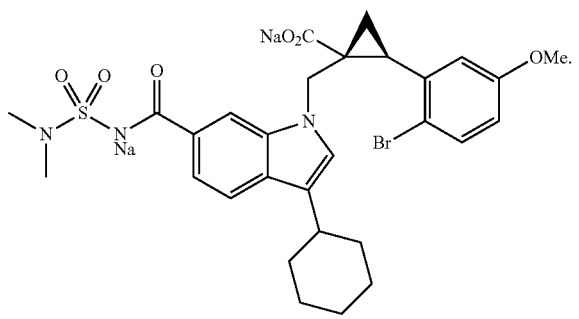

Another aspect of the invention is compound

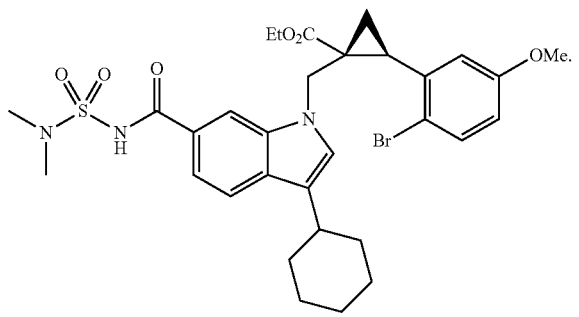 [SMILES: CCOC(=O)[C@]1(Cn2cc(C3CCCCC3)c3ccc(C(=O)NS(=O)(=O)N(C)C)cc32)C[C@H]1c1cc(OC)ccc1Br]

Another aspect of the invention is the compound

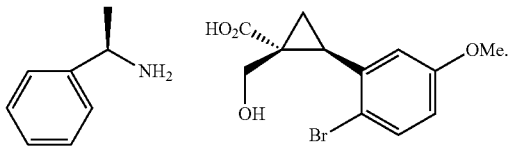

Another aspect of the invention is the compound

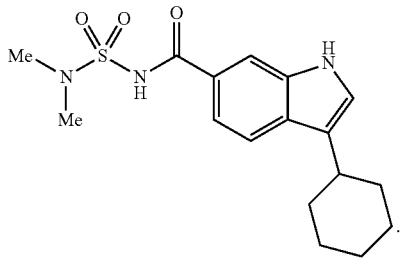 [SMILES: CN(C)S(=O)(=O)NC(=O)c1ccc2c(C3CCCCC3)c[nH]c2c1]

Another aspect of the invention is the compound

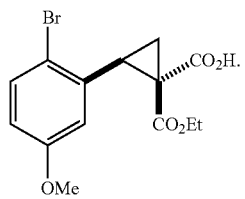

Another aspect of the invention is the compound

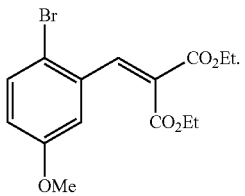 [SMILES: CCOC(=O)C(=Cc1cc(OC)ccc1Br)C(=O)OCC]

Synthetic Methods

The following methods are for illustrative purposes and are not intended to limit the scope of the invention. Those skilled in the art understand that there will be a number of equivalent methods for the preparation of these compounds and that the synthesis is not limited to the methods provided in the following examples. For example, some reagents and solvents may have equivalent alternatives known to those in the art. The variables describing general structural formulas and features in the synthetic schemes are distinct from and should not be confused with the variables in the claims or the rest of the specification. These variables are meant only to illustrate how to make some of the compounds of the invention. The following definitions are meant to serve as non-limiting examples to illustrate a term and are not meant to limit the definition to the examples listed.

Scheme 1 and 2 describe synthetic preparations for an indole intermediate.

Scheme 1.

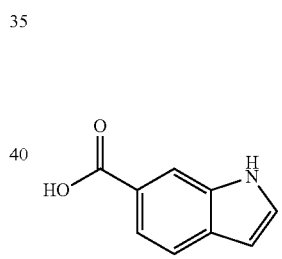

1) DMAP, DCM or THF, CDI
2) BOC$_2$O, DCM or THF
3) N,N-dimethylsulfamide DBU
4) IPA, NaOH
5) HCl, H$_2$O
6) Seed (optional), Filter
7) Water, Heptane (optional)

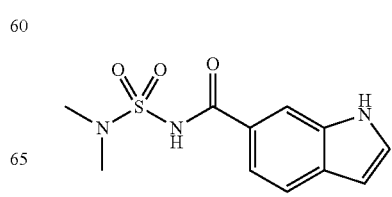

1) DCM, or toluene Cyclohexanone, Et$_3$SiH
2) TFA
3) Filter
4) Heptane

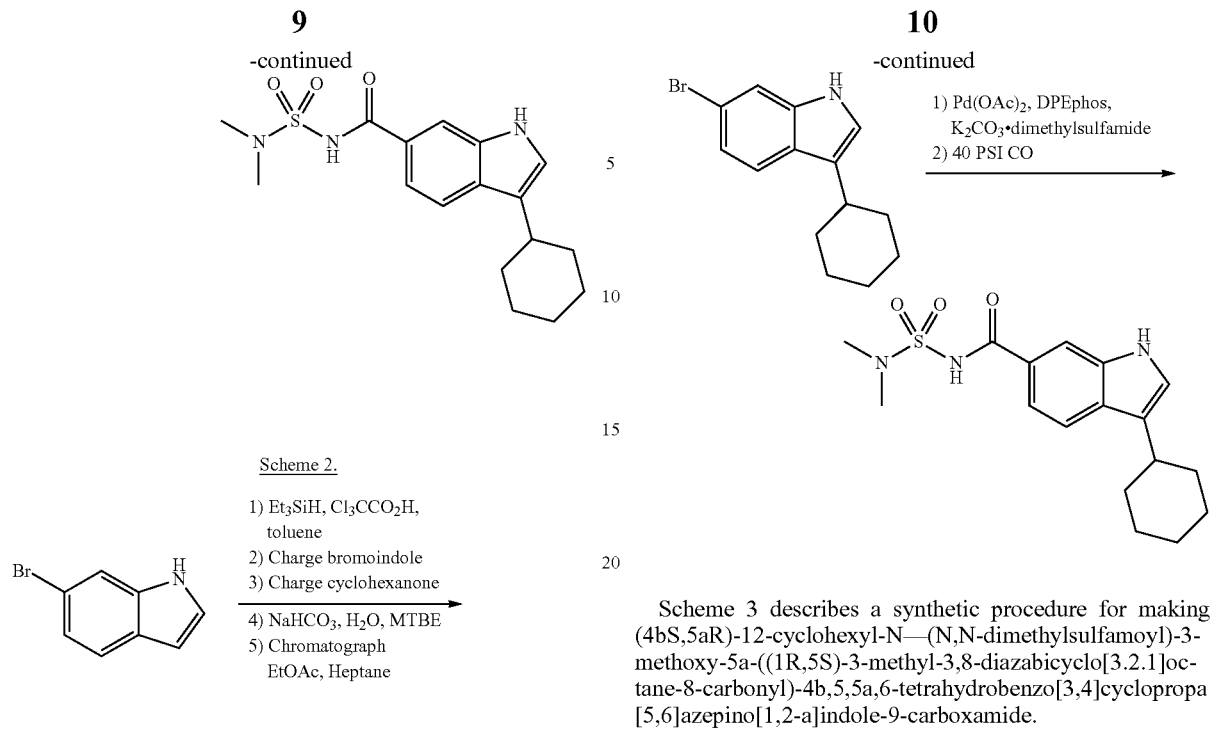
Scheme 3 describes a synthetic procedure for making (4bS,5aR)-12-cyclohexyl-N—(N,N-dimethylsulfamoyl)-3-methoxy-5a-((1R,5S)-3-methyl-3,8-diazabicyclo[3.2.1]octane-8-carbonyl)-4b,5,5a,6-tetrahydrobenzo[3,4]cyclopropa[5,6]azepino[1,2-a]indole-9-carboxamide.
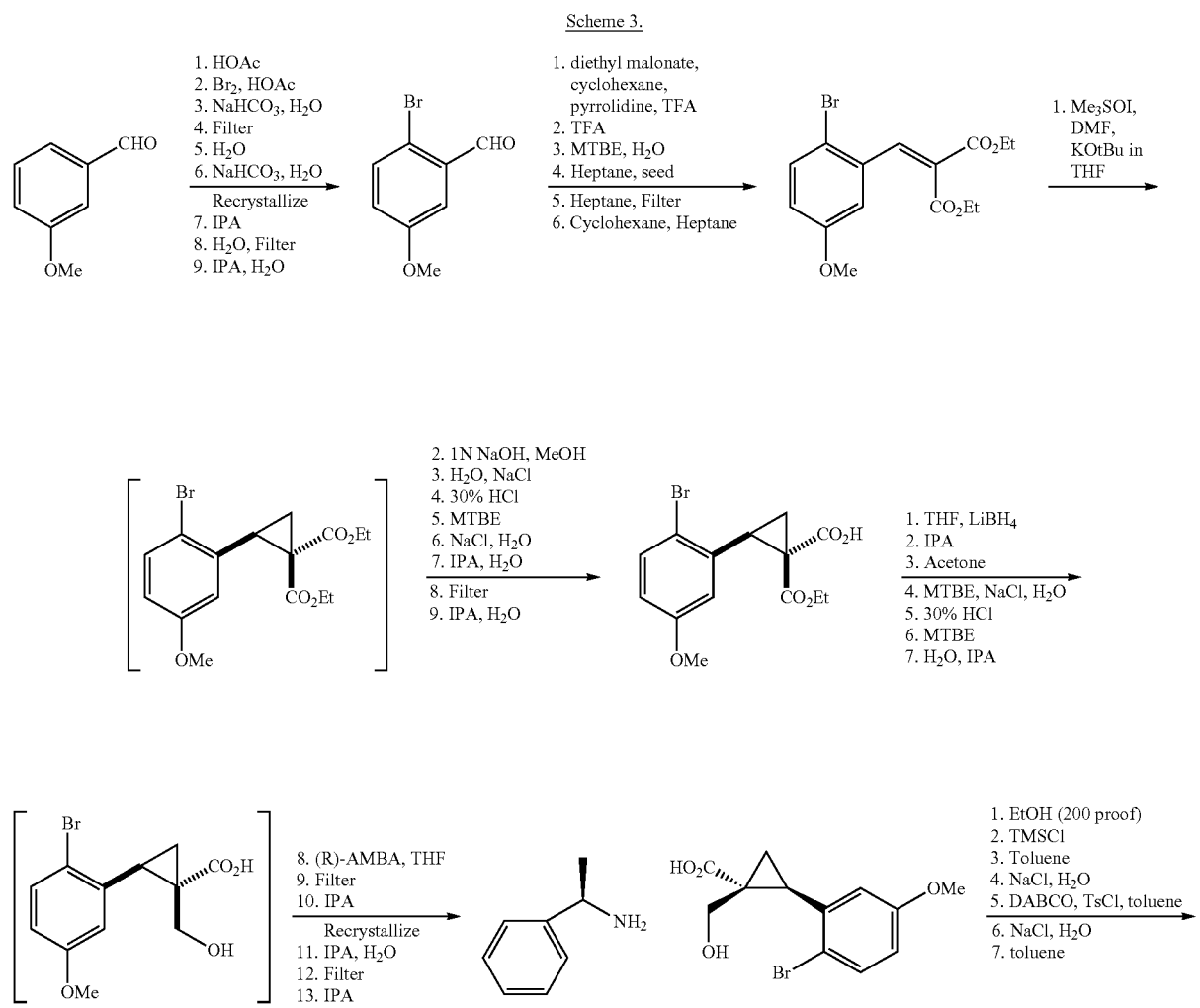

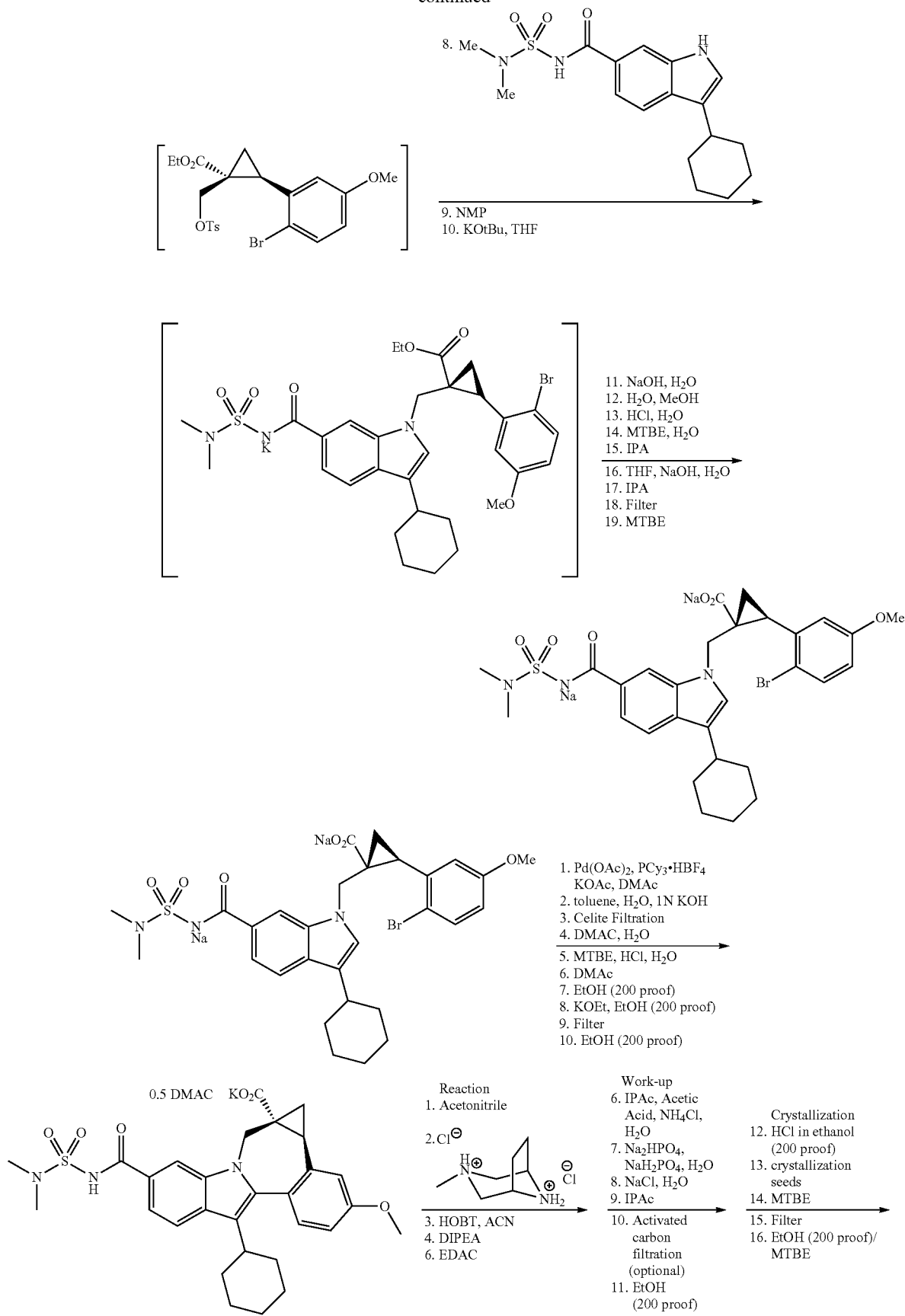

-continued

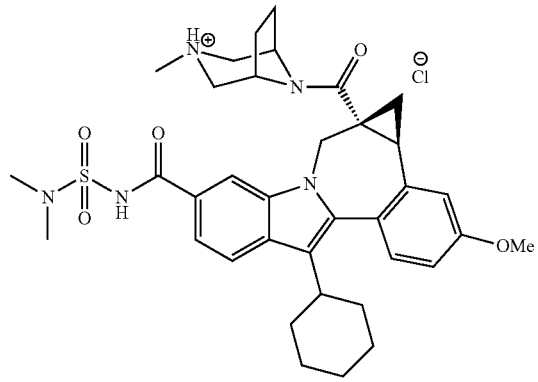

DESCRIPTION OF SPECIFIC EMBODIMENTS

Abbreviations used in the description generally follow conventions used in the art. Some abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for h or h, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Example 1

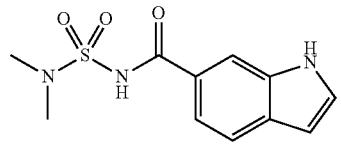 [SMILES: CN(C)S(=O)(=O)NC(=O)c1ccc2cc[nH]c2c1]

N—(N,N-dimethylsulfamoyl)-1H-indole-6-carboxamide

To a round bottom flask was charged 1H-indole-6-carboxylic acid (4 g) and 4-pyridinamine, N,N-dimethyl-(30.32 mg). Dichloromethane (28.40 mL) was charged, followed by 1, 1'-carbonyldiimidazole (4.31 g) in 3 portions over 15 minutes. Upon reaction completion di-t-butyldicarbonate (12.46 g) in dichloromethane (17.2 mL) was charged dropwise via an addition funnel over 45 minutes. Upon reaction completion N,N-Dimethylsulfamide (3.39 g) and 1,8-diazabicyclo[5.4.0]undec-7-ene (4.91 g) were charged. The mixture was heated at reflux until complete reaction conversion was achieved, cooled to 20° C., and stirred overnight. The solution was concentrated by distillation (until the pot temperature is 75° C.) and isopropyl alcohol (22.80 mL) and 10N sodium hydroxide (14.89 mL) were charged. The mixture was heated at 75° C. until reaction completion was achieved and then cooled to 40° C. Concentrated hydrogen chloride (43.02 mL) diluted with 40 mL of H$_2$O was charged dropwise. The mixture was heated to 50° C. for 1 h, cooled to 39° C., seeded and cooled to 23° C. After holding the slurry overnight it was filtered and the cake was washed twice with heptanes (25 mL) and placed in a vacuum oven. Solid (4.87 g) was isolated in 73.4% yield.

Alternative Synthesis of N—(N,N-dimethylsulfamoyl)-1H-indole-6-carboxamide

To a reactor with a nitrogen inlet and temperature probe was charged 1H-indole-6-carboxylic acid (1.00 kg, 6.21 mol, 1.00 equiv), N, N-dimethylaminopyridine (0.038 kg, 0.31 mol, 0.050 equiv), and tetrahydrofuran (7.00 L/kg, 6.22 kg/kg) followed by 1,1'-carbonyldiimidazole (1.03 kg, 6.21 mol, in 4×0.257 kg aliquots, 1.00 equiv corrected for potency). The mixture was held at 5-20° C. until reaction completion was achieved and then cooled to 5-10° C. Di-tert-butyldicarbonate (2.97 kg, 13.7 mol, 2.20 equiv) in THF (3 L/kg) was charged dropwise keeping the temperature between 2-8° C. The mixture was held at 5-20° C. until reaction completion was achieved. N,N-Dimethylsulfamide (0.865 kg, 6.83 mol, 1.10 equiv) was charged at 25±5° C. The mixture was aged for 0.5 h followed by addition of 1,8-diazabicyclo-undec-7-ene (1.24 kg, 8.07 mol, 1.30 equiv) keeping the temperature <35° C. The mixture was heated to 40° C., held until reaction completion was achieved, and distilled to 5-6 L/kg under vacuum (100-200 Torr) with a jacket temperature of 30-60° C. and a batch temperature of 30-45° C. Isopropanol (4 L/kg) was charged followed by 10 N sodium hydroxide (3.10 L, 31.0 mol, 5.00 equiv). The mixture was heated to 75±5° C., held until reaction completion was achieved and cooled to 20-22° C. Then 3N hydrochloric acid (~18 L/kg) was charged dropwise keeping the temperature <30° C. until pH 1-2 was achieved. The mixture was warmed to 35° C., held for 1 h, and cooled to 5-20° C. over at least 2 h. The slurry was held for 2 h at 5-20° C. and filtered. The reactor and cake were washed with water (2×5 kg) until a pH of 4-6 was reached.

The solid was dried at 45-50° C. until a KF of <0.5% was achieved to obtain 1.33 kg (80% yield) of N—(N,N-dimethylsulfamoyl)-1H-indole-6-carboxamide with an HPLC area percent purity ≥98.0 and HPLC wt %≥95.0. IR 3422, 3375, 3299, 2946, 1686, 1617, 1569, 1504, 1455, 1418, 1406, 1343, 1324, 1289, 1261, 1223, 1187, 1150, 1135, 1103, 1060, 978, 941, 898, 874, 818, 775, 733, 719, 660, 614 cm$^{-1}$; $^1$H NMR (400 MHz, DMSO-d6) δ 11.67 (s, 1H), 11.56 (s, 1H), 8.06 (s, 1H), 7.56-7.63 (m, 3H), 6.53 (s, 1H), 2.89 (s, 6H); $^{13}$C NMR (100 MHz, DMSO-d6) δ 167.2, 135.5, 131.7, 129.9, 124.7, 120.3, 119.5, 113.4, 102.1, 38.6; HRMS calculated for $C_{11}H_{14}O_3N_3S$: 268.07504. found 268.07489.

Example 2

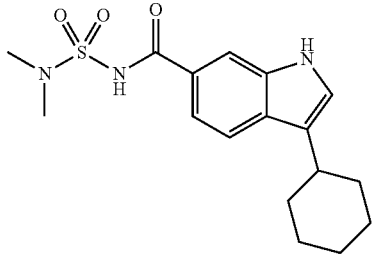 [SMILES: CN(C)S(=O)(=O)NC(=O)c1ccc2c(C3CCCCC3)c[nH]c2c1]

3-cyclohexyl-N—(N,N-dimethylsulfamoyl)-1H-indole-6-carboxamide

To a flask was charged N—(N,N-dimethylsulfamoyl)-1H-indole-6-carboxamide (1.5 g), dichloromethane (4.50 mL), cyclohexanone (1.17 mL) and triethylsilane (2.70 mL). The mixture was cooled to 5° C. and trifluoroacetic acid (1.27 mL) was charged keeping the temperature below 20° C. The mixture was stirred at 20° C. for 3 h and filtered. The solids were washed with heptane (2×10 mL) and the solid dried in a vacuum oven at 50° C. for 2 days to obtain a 69.4% yield.

Alternative Synthesis of 3-cyclohexyl-N—(N,N-dimethylsulfamoyl)-1H-indole-6-carboxamide To a reactor under nitrogen equipped with a temperature probe was charged N—(N,N-dimethylsulfamoyl)-1H-indole-6-carboxamide (1.00 kg, 3.74 mol, 1.00 equiv), toluene (3.00 L/kg, 2.61 kg/kg), cyclohexanone (0.734 kg, 7.48 mol, 2.00 equiv) and triethylsilane (1.30 kg, 11.2 mol, 3.00 equiv). The mixture was aged for 0.5 h at 18-22° C. and trifluoroacetic acid (1.29 kg, 11.2 mol, 3.00 equiv) was charged to the reactor over 20-30 minutes. The mixture was heated to 45° C., held until reaction completion was achieved and cyclohexane (3.00 L/kg, 2.35 kg/kg) was charged. The mixture was cooled to 10-20° C., held for 2 h, and the slurry filtered. The reactor and cake were rinsed with cyclohexane (1.0 L/kg, 0.78 kg/kg). The wet cake was transferred to a reactor, methanol (4.00 L/kg, 3.16 kg/kg) was charged, the mixture was heated to 45-50° C. and held for 30 minutes. Water (4.0 kg/kg) was charged at 45-50° C. and the mixture was cooled to 20-25° C. The slurry was filtered, the reactor and cake were washed with water (2×4 kg/kg) until pH 6-7 was reached. The solids were dried at 45-50° C. until a KF <0.2% was achieved to obtain 1.05 kg (80% yield) of 3-cyclohexyl-N—(N,N-dimethylsulfamoyl)-1H-indole-6-carboxamide with HPLC area percent purity ≥99.0 and HPLC wt %≥95.0. IR 3402, 3314, 2930, 2848, 1877, 1785, 1751, 1678, 1618, 1564, 1543, 1503, 1419, 1403, 1337, 1267, 1225, 1195, 1146, 1070, 977, 874, 827, 813, 771, 756, 737, 710, 667, 626 cm$^{-1}$; 1H NMR (600.13 MHz, DMSO-d6) δ 11.64 (s, 1H), 11.24 (br d, J=1.5 Hz, 1H), 8.01 (br d, J=1.0 Hz, 1H), 7.62 (d, J=8.5 Hz, 1H), 7.56 (dd, J=8.4, 1.5 Hz, 1H), 7.32 (d, J=2.3 Hz, 1H), 2.89 (s, 6H), 2.78 (m, 1H), 1.97 (m, 2H), 1.78 (m, 2H), 1.71 (m, 1H), 1.43 (m, 2H), 1.42 (m, 2H), 1.25 (m, 1H); 13C NMR (125.8 MHz, DMSO-d6) δ 166.7, 135.3, 129.6, 124.6, 123.9, 121.6, 118.3, 118.2, 112.8, 38.0, 34.8, 33.7, 26.4, 25.9; HRMS calculated for C17H24O3N3S: 350.1533. found 350.1529.

Example 3

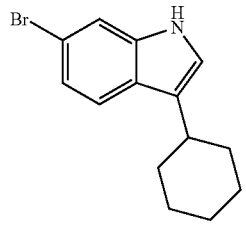 [SMILES: Brc1ccc2c(C3CCCCC3)c[nH]c2c1]

6-bromo-3-cyclohexyl-1H-indole

To a flask triethylsilane (3 equiv, 8.9 g), trichloroacetic acid (1.5 equiv, 6.3 g) and toluene (25.0 mL) were charged. The mixture was heated to 70° C. and a solution of 6-bromoindole (1.00 equiv, 5.0 g) and cyclohexanone (1.1 equiv, 2.8 g) in toluene was charged. The addition funnel was rinsed with 4 mL of toluene and stirred until reaction conversion reached completion. The mixture was cooled to 0° C., saturated NaHCO$_3$ solution and MTBE was charged and a phase split was conducted. The organic layer was dried with Na$_2$SO$_4$, filtered, concentrated and purified by column chromatography using 10% EtOAc in hexanes to afford 2.3 g of product.

Example 4

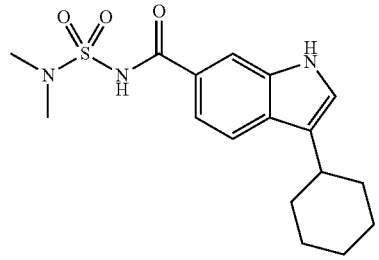 [SMILES: CN(C)S(=O)(=O)NC(=O)c1ccc2c(C3CCCCC3)c[nH]c2c1]

3-cyclohexyl-N—(N,N-dimethylsulfamoyl)-1H-indole-6-carboxamide

The ligand (DPEphos, 0.5 umol) was loaded into a vial and 50 uL of a 0.01 M solution of Pd(OAc)$_2$ (0.5 umol) was charged. The mixture was shaken for 0.5 h at 20° C. To the vial was charged 50 uL of a 0.2 M solution of 6-bromo-3-cyclohexyl-1H-indole (1.0 equiv, 10 umol) and 50 uL of a 0.6 M solution of N,N-dimethylsulfamide (3.0 equiv, 30 umol). The vial was concentrated to dryness and K$_2$CO$_3$ (3.0 equiv, 4.1 mg) was charged. The vial was equipped with a stirbar and 100 uL of toluene was charged. The vial was heated at 80° C. under 40 psi CO for 20 h. The vial was analyzed by HPLC for conversion.

Example 5

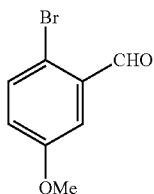 [SMILES: COc1ccc(Br)c(C=O)c1]

2-Bromo-5-methoxybenzaldehyde

The compound was made according to a literature method (Tetrahedron 1999, 10120). The following optional recrystallization was developed. To a 1 L round-bottom flask equipped with overhead stirring, reflux condenser and thermocouple was charged 2-bromo-5-methoxybenzaldehyde (50.0 g) and 250 mL 2-propanol. The slurry was warmed to 45° C. to give a clear, faint yellow solution. Water (250 mL) was then added via addition funnel over the course of 10 minutes while maintaining the internal temperature above 42° C. Note: A slurry forms upon addition of the first approximately ⅓ of the water charge. Once the addition was complete, heating was turned off and the slurry was cooled to ambient temperature (21° C.) over 1.5 h. After 2 h the slurry was filtered and the cake was subsequently washed with 2:1 water:2-propanol (65 mL). After air drying for 0.5 h, the solid (57 g) was dried in a vacuum oven (35° C., 4 mbar) for 16 h. 2-Bromo-5-methoxybenzaldehyde (46.77 g, 93.5% yield) was obtained as a white solid.

Example 6

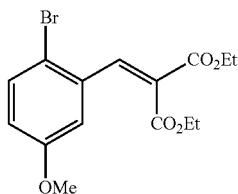 [SMILES: CCOC(=O)C(=Cc1cc(OC)ccc1Br)C(=O)OCC]

Diethyl 2-(2-bromo-5-methoxybenzylidene)malonate

To a 250 ml 3-neck flask equipped with Dean-Stark trap, bromo-5-methoxybenzaldehyde (43 g; 1.00 equiv; 199.96 mmoles) was charged. Diethyl malonate (35.5 g; 1.1 equiv; 217.31 mmoles), heptane (100 mL), pyrrolidine (1.4 g; 19.68 mmoles; 0.1 equiv), and acetic acid (1.2 g; 19.98 mmoles; 0.1 equiv) were charged. The mixture was heated to reflux and held until the reaction conversion reached completion. The mixture was cooled to 20° C., the upper heptane layer was removed and used "as is" in the next reaction.

Example 7

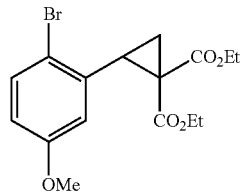 [SMILES: CCOC(=O)C1(C(=O)OCC)CC1c1cc(OC)ccc1Br]

Diethyl 2-(2-bromo-5-methoxyphenyl)cyclopropane-1,1-dicarboxylate

To a 500 ml 3-neck flask trimethylsulfoxonium iodide (48.4 g; 219.93 mmoles; 1.1 equiv) was charged (assuming the yield from the previous reaction is 100%). Dimethylformamide (100 mL), and potassium tert-butanol (220 mL; 220.00 mmoles; 1.1 equiv, as 1M THF solution) were charged. The reaction mixture was stirred at rt for 1 h. To this slurry, diethyl 2-(2-bromo-5-methoxybenzylidene)malonate was charged over 40 min while controlling the pot temperature below 30° C. The equipment was rinsed with DMF (50 mL). The reaction mixture was held at rt for 1 h and then used as is" in the next reaction.

Example 8

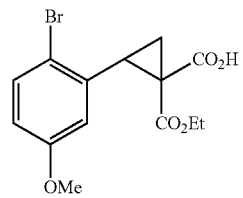 [SMILES: CCOC(=O)C1(C(=O)O)CC1c1cc(OC)ccc1Br]

2-(2-bromo-5-methoxyphenyl)-1-(ethoxycarbonyl) cyclopropane trans-carboxylic acid To the slurry of diethyl 2-(2-bromo-5-methoxyphenyl) cyclopropane-1,1-dicarboxylate (310 mL) MeOH (300 ml) was charged. 1N NaOH (300 mL) was charged and the reaction was stirred at rt until the reaction had less than 2% starting material remaining. Saturated brine (200 mL) was charged and the pH was adjusted from 14 to 3.5 with 37% HCl. The mixture was then extracted with MTBE (150 ml). The MTBE extraction was repeated, the organic layers were combined and extracted once with saturated brine (50 mL). The 400 mL of organic solution was vacuum distilled to a volume of 60 mL while controlling the temperature below 30° C. An oily residue formed during the concentration. IPA (80 mL) and water (50 mL) were charged and the mixture held at 25° C. for 16 h. The resulting slurry was filtered and washed with 20 ml of IPA. The cake was dried in a vacuum oven at 40° C. for 16 h and 2-(2-Bromo-5-methoxyphenyl)-1-(ethoxycarbonyl)cyclopropane carboxylic acid was obtained as a white solid (27 g, 20% overall yield). The mother liquor was stirred for 48 h and a second crop of 2-(2-bromo-5-methoxyphenyl)-1-(ethoxycarbonyl)cyclopropane carboxylic acid was obtained.

Alternative Synthesis of 2-(2-bromo-5-methoxyphenyl)-1-(ethoxycarbonyl)cyclopropane trans-carboxylic acid To 2-bromo-5-methoxybenzaldehyde (1 kg) was added cyclohexane (3 L), diethyl malonate (0.84 kg), trifluoroacetic acid (0.03 kg), and pyrrolidine (0.03 kg). The mixture was heated to 85° C. until reaction completion was achieved. Trifluoroacetic acid (0.03 kg) was charged and the mixture held at 75° C. for 2 h. Cool to 25° C. and charge MTBE (1.5 L) and water (1 L). The biphasic mixture was separated. The organic phase was washed with water (1 L) again, followed by vacuum distillative solvent exchange to 5 L of DMSO. Trimethylsulfoxonium iodide (1.2 kg) and potassium carbonate (1.6 kg) was charged and the mixture was heated to 55° C. until reaction completion was achieved. The mixture was cooled to 25° C. and filtered to afford product-rich filtrate. To the DMSO solution was added an aqueous 2.4 N solution of lithium hydroxide containing 0.23 kg lithium hydroxide. The mixture was held at 10° C. until reaction completion was achieved. To the mixture was charged water (5 L) and MTBE (2 L). The biphasic mixture was separated and the product-rich aqueous layer was neutralized with concentrated hydrochloric acid until a pH of 4.0 was obtained. The product was crystallized. The slurry was filtered and the cake was washed with water. The product was dried in vacuum at 40° C. until water content was less than 0.5 wt % analyzed by Karl Fisher to afford 1.32 kg off-white solid (83 M % overall yield) with HPLC area percent purity of 99 AP. $^1$H NMR (DMSO-$d_6$, 400 MHz) δ 7.48 (d, J=8.8 Hz, 1H), 6.8 (dd, J=8.8, 3.0 Hz, 1H), 6.7 (d, J=3.0 Hz, 1H), 3.67-3.83 (m, 6H), 3.07 (t, J=8.3 Hz, 1H), 2.22 (dd, J=8.1, 5.3 Hz, 1H), 1.64 (dd, J=9.1, 5.3 Hz, 1H), 0.72 (t, J=7.1 Hz, 3H); $^{13}$C NMR (DMSO-$d_6$, 100 MHz) δ 171.9, 158.2, 138.2, 132.3, 117.0, 116.1, 113.6, 62.3, 55.3, 34.1, 29.8, 14.7; IR (KBr pellet) 3087, 3018, 2987, 2960, 2911, 2840, 1749, 1666, 1598, 1569, 1471, 1422, 1383, 1293, 1269, 1228, 1170, 1154, 1053, 1015, 1001, 883, 874, 862, 850, 820, 744, 691, 681 cm$^{-1}$; Anal. calcd. for $C_{14}H_{15}BrO_5$: C, 49.00; H, 4.41; Br, 23.28. Found: C, 49.74; H, 4.52; Br, 23.44. HRMS calcd for $C_{14}H_{16}BrO_5$ [M+H]: 343.0181 found 343.0184.

Example 9

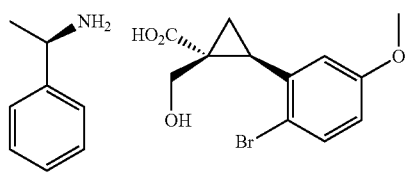

(R)-1-Phenylethanamine (1R,2R)-2-(2-bromo-5-methoxyphenyl)-1-(hydroxymethyl)cyclopropanecarboxylate To a 250 ml 3-neck flask was charged 2-(2-bromo-5-methoxyphenyl)-1-(ethoxycarbonyl)cyclopropane carboxylic acid (6.86 g). THF (20 mL) was charged followed by 20 mL of 2M LiBH$_4$ (2 eq.) which was charged slowly to control an appropriate rate of off-gassing. The mixture was warmed to 50° C. for 1 h, 5 ml of IPA was charged, and the mixture was held at 50° C. for until reaction completion was achieved. Half of the mixture was carried forward. To the mixture was slowly charged 20 ml of acidic half brine (made by mixing 10 mL brine+10 mL water+1.5 mL conc HCl) to the 25 mL of reaction mixture. The mixture was extracted with 2×20 mL of MTBE. The combined organic solution was vacuum distilled to a volume of 20 mL, 60 ml of 95% IPA/water was charged, and the distillation continued until the pot volume was 60 mL. The mixture was warmed to 60° C., and (R)-methylbenzylamine (0.9 g, 0.75 eq) was charged. The mixture was cooled to 40° C., held for 1 h, and cooled to rt. The slurry was held for 1 h, filtered and washed with 20 ml of IPA. The product was dried at 40° C. in a vacuum oven for 16 h to collect 1.3 g salt (31 M % yield), in 90% ee. (R)-1-Phenylethanamine (1R,2R)-2-(2-bromo-5-methoxyphenyl)-1-(hydroxyl methyl)cyclopropanecarboxylate (1.9 g) was dissolved in 15 ml of 90% IPA by warming to 80° C. The clear solution was cooled to 25° C. and the white slurry that forms was held for 1 h. The solid was filtered and washed with 10 ml of IPA. The solid weighed 1.6 g (85% yield) with 99.5% ee.

Alternative Synthesis of (R)-1-phenylethanaminium (1R,2R)-2-(2-bromo-5-methoxyphenyl)-1-(hydroxymethyl)cyclopropanecarboxylate To a reactor under nitrogen was added THF (7.2 L) and 2-(2-bromo-5-methoxyphenyl)-1-(ethoxycarbonyl)cyclopropane trans-carboxylic acid (1 kg). The solution was cooled to 0° C. To the mixture was added borane DMS complex (0.23 kg). The reaction mixture was held at 0° C. until reaction completion was achieved. To the above solution was added water (5 L). The mixture was cooled to 5° C. and neutralized with concentrated hydrochloric acid to pH 1~2. The resulting aqueous THF solution was concentrated in vacuum below 45° C. to afford a slurry. The slurry was filtered and the product was isolated, followed by water wash. To a 2$^{nd}$ reactor was charged 2-propanol (5.7 kg per kg of isolated product). Water was charged to adjust the 2-propanol:water ratio to 90:10 (vol/vol). The above mixture was heated to 65° C., followed by addition of (R)-methylbenzylamine (0.3 kg per kg of isolated product). The slurry was cooled to 15° C. and filtered on centrifuge to isolate the desired product with >90% ee. The above product was heated in 8 L of 2-propanol:water 90:10 at 80° C., followed by cooling to 15° C. to afford a white solid (0.5 kg, 41 M % yield) with chiral HPLC purity of 99.6% ee and potency 99.3~100.2 wt % after drying at 45° C. overnight. $^1$H NMR (DMSO-$d_6$, 400 MHz) δ 7.46 (br, d, J=7.3 Hz, 2H), 7.44 (d, J=8.7 Hz, 1H), 7.36 (br, t, J=7.8 Hz, 2H), 7.29 (br, t, J=7.4 Hz, 1H), 6.78 (d, J=3.0 Hz, 1H), 6.73 (dd, J=8.7, 3.0 Hz, 1H), 4.26 (q, J=6.7 Hz, 1H), 3.73 (s, 3H), 3.39 (d, J=11.1 Hz, 1H), 2.81 (d, J=11.2 Hz, 1H), 2.55 (t, J=7.5 Hz, 1H), 1.43 (d, J=6.7 Hz, 3H), 1.33 (dd, J=8.4, 4.1 Hz, 1H), 1.22 (dd, J=6.8, 4.2 Hz, 1H); $^{13}$C NMR (DMSO-$d_6$, 100 MHz) δ 177.0, 158.5, 142.3, 139.1, 132.6, 128.4, 127.6, 126.5, 116.8, 115.6, 113.6, 61.4, 55.3, 50.0, 31.6, 30.8, 22.3, 16.1; IR (KBr pellet) 3419, 2980, 2916, 2840, 2769, 2666, 2618, 2537, 1633, 1594, 1562, 1519, 1465, 1407, 1295, 1256, 1235, 1161, 1120, 1028, 1014, 850, 821, 813, 766, 698, 607 cm$^{-1}$; Anal. calcd. for $C_{20}H_{24}BrNO_4$: C, 56.88; H, 5.72; N, 3.31; Br, 18.92. Found: C, 56.90; H, 5.73; N, 3.45; Br, 19.26. HRMS calcd for free acid $C_{12}H_{14}BrO_4$ [M+H]: 299.9997 found 300.0011. Chiral HPLC analysis (Phenom Lux Cellulose-4 150×4.6 mm, 3 μm, buffer A=20/80 methanol/water (0.05% TFA), buffer B=20/80 methanol/acetonitrile (0.05% TFA), flow rate 1.00 mL/min, wavelength=220 nm), 99.6% ee, retention time=6.67 min (major), 8.09 min (minor); Optical rotation $[\alpha]_D^{20}$ –14.92° (c=3.86 methanol).

Example 10

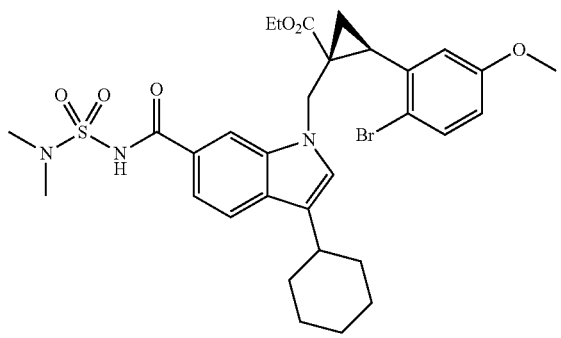

(1R,2R)-ethyl 2-(2-bromo-5-methoxyphenyl)-1-((3-cyclohexyl-6-(N,N-dimethylsulfamoylcarbamoyl)-1H-indol-1-yl)methyl)cyclopropanecarboxylate To a 10 L reactor was charged (R)-1-phenylethanamine (1R,2R)-2-(2-bromo-5-methoxyphenyl)-1-(hydroxymethyl) cyclopropanecarboxylate (304 g, 0.72 mol) and 4 L of ethanol. To the mixture was charged 300 mL (2.4 mol) of TMSCl and the mixture was heated to 63° C. for 15 h. The reaction was cooled to 20° C., toluene (4 L) was charged and the mixture was distilled at 105 torr to a volume of 2 L. Toluene (2.4 L) and half brine (3.6 L) was charged. The phases were split and the toluene layer was washed with half brine (2.4 L). The toluene layer was washed with water (1.2 L). The toluene layer was distilled at 105 torr to reduce volume to 1.5 L. DABCO was charged as a solid into the reaction mixture (123 g, 1.10 mol), stirred to dissolve, and the reaction was cooled to –5° C. To the mixture TsCl (152 g, 0.80 mol) in toluene (1.1 L) was charged at –5° C. to 5° C. The mixture was warmed to 20° C. and stirred for 1 h, followed by the addition of half brine (2.4 L). The mixture was held at 20° C. for 2 h and after a phase split the organic phase was washed with 2.4 L half brine solution. After a phase split the organic layer was washed with 1.2 L water. After a phase split, 0.9 L toluene was charged and the mixture was distilled at 105 torr to reduce the volume to 0.8 L. At 20° C.-40° C. 3-cyclohexyl-N—(N,N-dimethylsulfamoyl)-1H-indole-6-carboxamide (282.1 g, 0.81 mol) was charged. DMF (1.7 L) was charged and stirred until homogenous. At 20-40° C., 1 M NaHMDS/THF solution (780 mL, 0.78 mol) was charged and the mixture was heated to 40-60° C. Additional 1 M NaHMDS/THF solution (150 mL, 0.15 mol) was charged. At 60° C., add 1 M NaHMDS/THF solution (545 mL, 0.545 mol). The mixture was stirred at 60° C. for 5 h, cooled to 20° C. and 3.65 L MTBE was charged. To the mixture 3.35 L 1 N HCl was charged below 40° C. After holding at 40° C. for 2 h, the mixture was cooled to 20° C. and a phase split was conducted. The organic layers were washed 3×3.5 L water, distilled under atmospheric pressure to ca. 1.5 L and 3 L IPA was charged. The mixture was distilled to ca. 1.4 L and 1.3 L IPA was charged. The mixture was cooled to 40° C. and 1.5 g of seeds were charged. The slurry was held at 40° C. for 30 min and 2.7 L heptane was charged at 40° C. The slurry was cooled to 20° C., held overnight and filtered. The cake was washed with 600 mL IPA:heptane (1:1) followed by 2×600 mL of heptanes. Wet cake was 413 g. A 10 g sample of wet cake was removed and the remaining cake was dried under vacuum at 40° C. for 16 h obtaining 346 g of product (74%), 99.2 HPLC area percent purity. To a flask was charged (1R,2R)-ethyl 2-(2-bromo-5-methoxyphenyl)-1-((3-cyclohexyl-6-(N,N-dimethylsulfamoyl-carbamoyl)-1H-indol-1-yl)methyl)cyclopropane carboxylate (35 g) and IPA (245 mL). The mixture was heated to 80° C., cooled to 40° C., and held for 0.5 h. The slurry was cooled to rt and filtered. The wet cake was charged to a flask and IPA (280 mL) was charged. The mixture was heated to 80° C., cooled to 40° C., and held for 0.5 h. The slurry was cooled to rt and filtered. The cake was washed with IPA (40 mL) twice and with heptane (60 mL) twice. After drying under vacuum at 40° C. for 16 h, 28.1 g (80%) of solid was obtained in 99.6 HPLC area percent purity.

Example 11

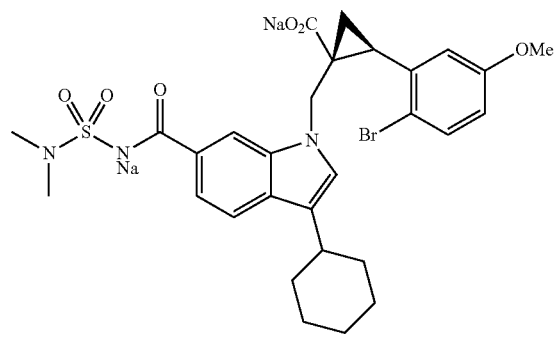

Sodium (1-(((1R,2R)-2-(2-bromo-5-methoxyphenyl)-1-carboxylatocyclopropyl)methyl)-3-cyclohexyl-1H-indole-6-carbonyl)(N,N-dimethylsulfamoyl)amide To a 20 L reactor was charged (R)-1-phenylethanamine (1R,2R)-2-(2-bromo-5-methoxyphenyl)-1-(hydroxymethyl) cyclopropanecarboxylate (300 g, 0.71 mol) and 2.55 L ethanol. To the mixture was charged 300 mL (2.4 mol) TMSCl followed by 0.15 L ethanol. The reaction mixture was heated to 60° C. for 5 h and cooled to 20° C. Toluene (2.7 L) was charged and the mixture distilled at 70 torr to 1.5 L. Toluene (1.8 L) and 5 wt % aqueous KCl (3.0 L) were charged. The phases were split at 40° C. and the toluene layer was washed with 5 wt % aqueous KCl (3.0 L) at 40° C. After a phase split, the toluene layer was washed with water (1.2 L) and the phases split at 40° C. DABCO (142 g, 1.27 mol) and additional toluene (2.4 L) were charged. Distillation at 70 torr reduced the volume to 1.2 L and toluene (1.5 L) was charged. After cooling the reaction to –5° C., TsCl (149 g, 0.78 mol) was charged as a solid to the reactor followed by toluene (0.6 L). The mixture was warmed to 20° C., stirred for 1 h and 5 wt % aqueous KCl. Additional toluene (2.4 L) was charged. After stirring at 40° C. for 2 h the phases were split. The toluene layer was washed with 5 wt % aqueous KCl (2.4 L) and the phases split at 40° C. The toluene layer was washed with water (1.2 L) and the phases split at 40° C. Additional toluene (2.4 L)

was charged, the mixture distilled at 50 torr to reduce the volume to 1.2 L, and 3-cyclohexyl-N—(N,N-dimethylsulfamoyl)-1H-indole-6-carboxamide (290.4 g, 0.83 mol) was charged followed by 1.8 L N-methyl-2-pyrrolidone (NMP). The mixture was stirred until homogenous and at 20-30° C., 1 M t-BuOK/THF solution (748 mL, 0.75 mol) was charged followed by THF (0.075 L). At 60° C., 1 M t-BuOK/THF solution (mL, 0.75 mol) was charged over 0.5 h followed by THF (0.075 L). The mixture was stirred at 60° C. for 2 h and then cooled to 50° C. Water (0.15 L), 10N aqueous NaOH (0.20 L, 2.0 mol), water (0.15 L), and then MeOH (0.30 L) were charged. The mixture was stirred at 50° C. for 1.5 h, cooled to 20° C., and 2N HCl (2.13 L) was charged followed by MTBE (2.4 L). The phases were split. The toluene/MTBE layer was washed with water and phase split three times (3×2.4 L). The organic layer was distilled at 70 torr to ca. 1.2 L. IPA (0.9 L) was charged distilled at 70 torr to 1.2 L a total of six. The stream was diluted with THF (5.3 L), heated to 60° C., and 10 N NaOH (82.4 mL, 0.82 mol) was charged followed by THF (75 mL). The batch was seeded with sodium (1-(((1R,2R)-2-(2-bromo-5-methoxyphenyl)-1-carboxylatocyclopropyl)methyl)-3-cyclohexyl-1H-indole-6-carbonyl)(N,N-dimethylsulfamoyl)amide (1.5 g) followed by THF (210 mL). The slurry was held for 0.5 h at 60° C. Additional 10 N NaOH (45.5 mL, 0.46 mol) was charged over 0.5 h followed by THF (75 mL). IPA (0.90 L) was charged over 15 minutes. The slurry was held at 60° C. for 0.5 h, cooled to 20° C. over 1 h, held at 20° C. for 15 h and filtered. The cake was washed with 2×1.2 L MTBE and dried under vacuum at 50° C. for 24 h. A white solid (333.1 g) was obtained (0.49 mol, 69% yield) in 99.4 HPLC area percent purity. $^1$H NMR (DMSO-$d_6$, 400 MHz) δ 7.96 (s, 1H), 7.66 (d, J=8.3 Hz, 1H), 7.53 (d, J=8.8 Hz, 1H), 7.37 (d, J=8.3 Hz, 1H), 6.87-6.65 (m, 3H), 4.95 (d, J=14.1 Hz, 1H), 3.47 (s, 3H), 3.30 (d, J=14.1 Hz, 1H), 2.75 (t, J=7.6 Hz, 1H), 2.75 (m, 1H), 2.62 (s, 6H), 2.03-1.65 (m, 5H), 1.53 (m, 1H), 1.45-1.15 (m, 5H), 1.0 (m, 1H); $^{13}$C NMR (DMSO-$d_6$, 100 MHz) δ 176.5, 172.0, 158.8, 139.5, 136.2, 132.9, 132.0, 127.9, 125.8, 119.4, 119.0, 116.9, 116.8, 116.0, 114.0, 110.8, 55.4, 45.0, 38.9, 35.0, 33.7, 33.6, 32.0 (2 peaks), 26.5, 26.1, 16.1; IR (KBr pellet) 3436, 2924, 2846, 1631, 1569, 1469, 1398, 1339, 1248, 1168, 1109, 949, 834, 712 cm$^{-1}$; HRMS (ESI) calcd for $C_{29}H_{33}O_6N_3BrNa_2S$ [M+H]: 676.10633 found 676.10693.

Example 12

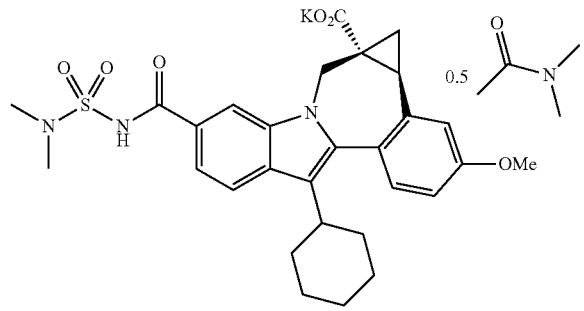

Potassium (4bS,5aR,12aR)-12-cyclohexyl-9-((N,N-dimethylsulfamoyl) carbamoyl)-3-methoxy-4b,5,5a,6-tetrahydrobenzo[3,4]cyclopropa[5,6]azepino-[1,2-a]indole-5a-carboxylate hemi-N,N-dimethylacetamide solvate To a 500 ml 3-neck flask, (1R,2R)-ethyl 2-(2-bromo-5-methoxyphenyl)-1-((3-cyclohexyl-6-(N,N-dimethylsulfamoylcarbamoyl)-1H-indol-1-yl)methyl)cyclopropanecarboxylate (10 g), KHCO$_3$ (6.0 g), Pd(OAc)$_2$ (0.18 g) and PCy$_3$-HBF$_4$ (0.6 g) was charged. DMAC (100 mL) and toluene (100 mL) were charged then the mixture is degassed 3 times by applying vacuum with agitation and refilling with nitrogen. The mixture was heated to reflux at 125-127° C. for 3-5 h and then cooled to 25° C. and water (60 mL) was added. KOH (3.0 g, purity 85%, 3 eq) was charged and the mixture stirred at 35-40° C. for 1 h. The reaction mixture was filtered on a Celite Pad and the phases were split discarding the toluene layer. To the aqueous/DMAC layer, MTBE (100 mL) was charged. The mixture was acidified with 37% HCl to a pH of 2-3. The phases were split and the aqueous layer was extracted with MTBE (50 mL). The MTBE layers were combined and distilled at atmosphere pressure until the pot temperature increased to 70° C. To the mixture, 200 Proof EtOH (80 mL) was charged, the reaction temperature was adjusted to 50° C., and 24% KOEt (5.35 g, 1 eq.) was slowly charged. The mixture was then cooled to RT (20-23° C.), stirred at rt for 1 h and the slurry filtered. The cake was washed twice with EtOH (10 mL) and the wet cake (11.6 g) was dried at 60° C. under vacuum for 16 h with a N$_2$ stream. This afforded 6.81 g white crystalline solid. (70% yield) as the DMAC solvated K salt in 99.1 HPLC area percent purity at 254 nm (KF=0.86%, LOD<1%, Pd=70 ppm).

Alternative synthesis of potassium (4bS,5aR,12aR)-12-cyclohexyl-9-((N,N-dimethylsulfamoyl)carbamoyl)-3-methoxy-4b,5,5a,6-tetrahydrobenzo[3,4]cyclopropa[5,6]azepino[1,2-a]indole-5a-carboxylate hemi-N,N-dimethylacetamide solvate To a 250 ml 3-neck flask, was charged sodium (1-(((1R,2R)-2-(2-bromo-5-methoxyphenyl)-1-carboxylatocyclopropyl)methyl)-3-cyclohexyl-1H-indole-6-carbonyl)(N,N-dimethylsulfamoyl)amide (10 g), tetramethylammonium acetate (4.72 g), palladium acetate (0.13 g), tricyclohexylphosphine tetrafluoroborate (0.54 g) and (50 mL) dimethylacetamide (DMAc). The mixture was degassed three times by applying vacuum with agitation and refilling with nitrogen. The mixture was heated to 110° C. until reaction completion was achieved. The mixture was cooled to 25° C. and water (90 mL) was added. Aqueous potassium hydroxide (45 wt %, 2.76 g) was charged, the mixture was stirred at 25° C. for 1 h, after which 70 mL of methyl tert-butyl ether (MTBE) was added. The biphasic reaction mixture was filtered through a plug of celite and the phases were split discarding the MTBE layer. To the aqueous rich layer, was charged MTBE (110 mL), 200 proof absolute ethanol (30 mL) and 37 wt % HCl (8.60 g). The phases were split. The MTBE rich layer was washed two times with water (50 mL). DMAc (9 mL) was charged and the mixture was concentrated by distilling at atmosphere pressure until the pot temperature increased to >70° C. When the distillation was complete, the temperature was reduced to 50° C. and EtOH (70 mL) was added. At 50° C., 24 wt percent potassium ethoxide in ethanol solution (5.18 g) was charged over 2 h. After the addition, the slurry was cooled to 25° C. over 1 h and aged at 25° C. for 2 h. The solid was filtered and washed consecutively with EtOH (40 mL) and MTBE (40 mL). The product was dried at 65° C. under vacuum for 12 hours with a nitrogen stream. This afforded 7.48 g of a white crystalline solid (80% yield) as the hemi-DMAc solvated mono-potassium salt. 1H NMR (DMSO-d6, 500 MHz) δ 7.65-8.33 (2H, m), 6.98-7.25 (2H, m), 5.13-5.38 (1H, m), 3.84-3.91 (2.5H, m), 3.35-3.44 (0.25H, m), 2.66-2.94 (7.4H, m), 1.20-2.02 (9H, m), 0.06 (0.4H, m) ppm; 13C NMR (DMSO-d6, 125 MHz) δ 173.9, 173.5, 169.6, 159.3, 159.0, 139.2, 137.0, 135.2, 134.9, 132.3, 132.2, 127.6, 122.6, 120.0, 119.1, 119.0, 117.7, 117.5, 117.1, 117.0, 113.2, 112.2, 111.7, 109.6, 56.0, 55.2, 44.3, 38.7, 36.1, 30.5, 26.7, 25.6, 21.3, 18.5, 13.6 ppm; IR (KBr pellet) 3436, 2926, 2846, 1665, 1611, 1568, 1458, 1359, 1264, 1158, 1077 cm-1; Chiral HPLC analysis (Chiracel OJ-RH 150×4.6 mm, 5 μm, 53% methanol/water (0.05 wt % TFA), 45° C. column temperature, flow rate 1.00 mL/min, λ=260 nm), 99.5% ee, retention time=12.06 min (minor), 14.45 min (major); Elemental analysis 56.8% C, 6.1% H, 7.3% N, 4.5% S, 5.7% K; Optical rotation [α]D20−160.23° (c=1.3 methanol); HRMS (Orbitrap) calcd for C29H34O6N3S [M+H]: 552.21628 found 552.21637.

Example 13

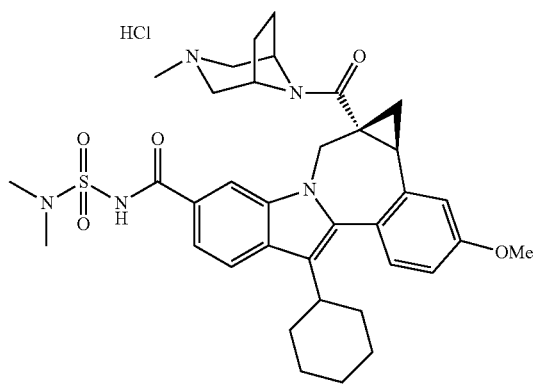 [SMILES: COc1ccc2c(c1)[C@@H]1C[C@]1(C(=O)N1C3CCC1CN(C)C3)Cn1c-2c(C2CCCCC2)c2ccc(C(=O)NS(=O)(=O)N(C)C)cc21 ; Cl]

(4bS,5aR)-12-cyclohexyl-N—(N,N-dimethylsulfamoyl)-3-methoxy-5a-((1R,5S)-3-methyl-3,8-diazabicyclo[3.2.1]octane-8-carbonyl)-4b,5,5a,6-tetrahydrobenzo[3,4]cyclopropa[5,6]azepino[1,2-a]indole-9-carboxamide hydrochloride To an inert, glass-lined reactor equipped with an overhead stirrer was charged acetonitrile (8 L). With the agitator set to 150 RPM, the reactor was charged with potassium (4bS,5aR,12aR)-12-cyclohexyl-((N,N-dimethylsulfamoyl)carbamoyl)-3-methoxy-4b,5,5a,6-tetrahydrobenzo[3,4]cyclopropa[5,6]azepino[1,2-a]indole-5a-carboxylate hemi-N,N-dimethylacetamide solvate (1000 g, 1.69 mol, 1.0 equiv), (1R,5S)-3-methyl-3,8-diazabicyclo[3.2.1]octane (388.3 g, 1.95 mol, 1.15 equiv), HOBt hydrate (298.6 g, 1.95 mol, 1.15 equiv), and EDAC (373.8 g, 1.95 mol, 1.15 equiv); the third solid charge was chased with acetonitrile (1 L). The temperature of the reaction mixture was adjusted to 20° C., and then N,N-diisopropylethylamine (657.5 g, 5.09 mol, 3.0 equiv) was introduced to the mixture while maintaining the internal temperature ≤27.5° C. The base charge was chased with an additional aliquot of acetonitrile (1 L), and the resulting mixture was aged at room temperature for 12 h.

Upon reaction completion 2.5% starting material remaining) isopropyl acetate (10 L) was introduced, followed by saturated ammonium chloride solution (5 L, 5 vol), glacial acetic acid (575 g, 8.45 mol, 5.0 equiv) and water (5 L, 5 vol). The resulting mixture was agitated at 20-25° C. for 15 min, then left to settle for 15 min, and the aqueous layer was discharged. The organic layer was then treated with a solution of pH 7 KH2PO4/K2HPO4 buffer solution (12.5 L, 12.5 vol), the mixture was agitated at 20° C.≤T≤25° C. for 15 min, then left to settle for 15 min, and the resulting aqueous layer was discharged. The organic layer was then treated with a second portion of pH 7KH2PO4/K2HPO4 buffer solution (12.5 L, 12.5 vol), the mixture was agitated at 20-25° C. for 15 min, then left to settle for 15 min, and the resulting aqueous layer was discharged. The product-rich organic layer was treated with a mixture of brine (5 L, 5 vol) and water (5 L, 5 vol). The resulting mixture was agitated at 20-25° C. for 15 min, then left to settle for 15 min, and the aqueous layer was discharged. The organic solution was then concentrated to approx. 7.5 L (100-300 mbar, T≤50° C.), and subsequently subjected to constant volume distillation, in order to reduce the water content to ≤1000 ppm (IPC, KF). Absolute ethanol was charged (7.5 L), and constant volume distillation was continued (100-300 mbar, T≤50° C.) until the IPAc level was reduced to ≤1% (as determined by GC). The reaction temperature was adjusted to 30-35° C., and the solution was subjected to polish filtration. The clarified solution was further concentrated (100-300 mbar, T≤50° C.) to a final volume of 10 L (10 volumes). The batch temperature was adjusted to 20° C., and ethanolic HCl (970 g of a 1.2 M solution, 1.2 equiv) was introduced, followed by (4bS,5aR)-12-cyclohexyl-N—(N,N-dimethylsulfamoyl)-3-methoxy-5a-((1R,5S)-3-methyl-3,8-diazabicyclo[3.2.1]octane-8-carbonyl)-4b,5,5a,6-tetrahydrobenzo[3,4]cyclopropa[5,6]azepino[1,2-a]indole-9-carboxamide hydrochloride seeds (10 g). After holding for 1 h at 20-25° C., MTBE (10 L, 10 vol) was introduced over 1 h. The resulting slurry was aged at 25-30° C. for 12 h, and then 20-25° C. for 12 h. The slurry was discharged to a filter, the derived wet cake was washed with 2:1 MTBE:EtOH (2×3 L), and then deliquored on the filter under vacuum with a nitrogen bleed. The material was transferred from the filter to trays and dried in the oven (full house vacuum, T≤50° C.) until KF ≤4% and MTBE and ethanol levels were ≤0.5% (wt/wt).

Alternative procedure for (4bS,5aR)-12-cyclohexyl-N—(N,N-dimethylsulfamoyl)-3-methoxy-5a-((1R,5S)-3-methyl-3,8-diazabicyclo[3.2.1]octane-8-carbonyl)-4b,5,5a,6-tetrahydrobenzo[3,4]cyclopropa[5,6]azepino[1,2-a]indole-9-carboxamide hydrochloride To an inert, glass-lined 1-L reactor equipped with an overhead stirrer were charged (4bS,5aR,12aR)-12-cyclohexyl-((N,N-dimethylsulfamoyl)carbamoyl)-3-methoxy-4b,5,5a,6-tetrahydrobenzo[3,4]cyclopropa[5,6]azepino[1,2-a]indole-5a-carboxylate hemi-N,N-dimethylacetamide solvate (20 g, 29.4 mmol, 1.0 equiv), (1R,5S)-3-methyl-3,8-diazabicyclo[3.2.1]octane (6.45 g, 32.4 mmol, 1.1 equiv), 1-hydroxybenzotriazole hydrate (approximately 20 wt % water; 5.64 g, 33.5 mmol, 1.14 equiv), acetonitrile (180 mL, 9 L/kg), and N,N-diisopropylethylamine (10.5 g, 81.0 mmol, 2.75 equiv). The mixture was stirred at 20-25° C. for 1 h. To the reactor was then charged 1-ethyl-3-(3-dimethylaminopropyl)carbodiimide hydrochloride (6.49 g, 33.9 mmol, 1.15 equiv), which was chased with acetonitrile (20 mL, 1 L/kg).

The resulting mixture was aged at 20-25° C. for 18 h. Upon reaction completion 2.5% starting material remaining) isopropyl acetate (200 mL, 10 L/kg) was introduced, followed by glacial acetic acid (8.86 g, 147 mmol, 5.0 equiv), saturated ammonium chloride solution (100 mL, 5 L/kg), and water (100 mL, 5 L/kg). The resulting mixture was agitated at 20-25° C. for 0.5 h, then left to settle for 15 min, and the aqueous layer was discharged. The organic layer was then treated with a solution of pH 7 $KH_2PO_4/K_2HPO_4$ 1 M buffer solution (250 mL, 12.5 L/kg), the mixture was agitated at 20-25° C. for 0.5 h, then left to settle for 15 min, and the resulting aqueous layer was discharged. The organic layer was then treated with a second portion of pH 7 $KH_2PO_4/K_2HPO_4$ 1 M buffer solution (250 mL, 12.5 L/kg), the mixture was agitated at 20-25° C. for 0.5 h, then left to settle for 15 min, and the resulting aqueous layer was discharged. The product-rich organic layer was treated with a mixture of saturated sodium chloride (100 mL, 5 L/kg) and water (100 mL, 5 L/kg). The resulting mixture was agitated at 20-25° C. for 0.5 h, then left to settle for 15 min, and the aqueous layer was discharged. The organic solution was then concentrated to approximately 7.5 L/kg at ≤100 mbar, 20-25° C. and subsequently subjected to constant volume distillation by adding isopropyl acetate (300 mL, 15 L/kg), in order to reduce the water content to ≤1000 ppm. The stream was diluted with isopropyl acetate (60 mL, 3 L/kg) and subjected to polish filtration, and the filter train was rinsed with isopropyl acetate (60 mL, 3 L/kg). The resulting stream was transferred to a clean, glass-lined 1-L reactor, concentrated to approximately 10 L/kg at 100 mbar, 20-30° C., and subjected to constant volume distillation by adding absolute ethanol (770 mL, 38.5 L/kg) at 100 mbar, 20-30° C., until the IPAc level was reduced to ≤1 volume percent. The batch temperature was adjusted to 40-45° C., and ethanolic HCl (24.7 mL of a 1.25 M solution, 30.9 mmol, 1.05 equiv) was added, followed by (4bS,5aR)-12-cyclohexyl-N—(N,N-dimethylsulfamoyl)-3-methoxy-5a-((1R,5S)-3-methyl-3,8-diazabicyclo[3.2.1]octane-8-carbonyl)-4b,5,5a,6-tetrahydrobenzo[3,4]cyclopropa[5,6]azepino[1,2-a]indole-9-carboxamide hydrochloride seeds (0.2 g, 1.0 wt %). After holding for 22 h at 40-45° C., methyl tert-butyl ether (MTBE) (466 mL, 23.3 L/kg) was added over 14 h by addition pump. The resulting slurry was aged at 40-45° C. for 2 h, then cooled to 20° C. over 2 h. The slurry was discharged to a filter and the derived wet cake was washed with 2:1 MTBE:EtOH (1×80 mL, 4 L/kg) and MTBE (1×80 mL, 4 L/kg). The material was dried in a vacuum oven at 50° C. until ethanol was ≤0.7 wt % and MTBE ≤0.5 wt % to afford the desired product (18.04 g, 88% yield). $^1$H-NMR (600.13 MHz, $CD_3CN/D_2O$ 10/1 v/v) major rotamer: 7.91 (1H, br s), 7.90 (1H, d, J=8.5 Hz), 7.55 (1H, br d, J=8.5 Hz), 7.29 (1H, d, J=8.5 Hz), 7.20 (1H, d, J=2.5 Hz), 7.00 (1H, dd, J=8.5 Hz, 2.7 Hz), 5.03 (1H, br d, J=12.7 Hz), 4.58 (2H, br d, J=4.9 Hz), 3.87 (3H, s), 3.56 (1H, d, J=15.5 Hz), 3.40 (3H, br s), 3.32-3.28 (4H, m), 2.96 (6H, s), 2.92 (1H, tt, J=12.2 Hz, 3.6 Hz), 2.59 (1H, br t, J=7.0 Hz), 2.05-1.90 (2H, m), 1.79-1.71 (4H, m), 1.55 (2H, br d, J=12.2 Hz), 1.46-1.36 (4H, m), 1.26 (2H, t, J=5.3 Hz), 1.23-1.15 (2H, m); minor rotamer: 8.05 (1H, br s), 7.92 (1H, d, J=8.5 Hz), 7.58 (1H, dd, J=8.5 Hz, 1.4 Hz), 7.34 (1H, d, J=8.5 Hz), 7.15 (1H, d, J=2.6 Hz), 6.98 (1H, d, overlap with major rotamer), 4.91 (1H, d, J=15.0 Hz), 4.58 (2H, br d, J=4.9 Hz), 4.11 (1H, d, J=15.0 Hz), 3.89 (3H, s), 3.46 (2H, br d, J=12.5 Hz), 3.17 (2H, br d, J=12.5 Hz), 2.97 (6H, s), 2.85 (3H, br s), 2.76 (1H, tt, J=12.1 Hz, 3.5 Hz), 2.49 (1H, br s), 2.05-1.90 (2H, m), 1.79-1.71 (4H, m), 1.46-1.36 (6H, m), 1.23-1.15 (2H, m), 1.10 (1H, m), 0.03 (1H, t, J=6.1 Hz). $^{13}$C-NMR (125.8 MHz, $CD_3CN/D_2O$ 10/1 v/v) major rotamer: 170.1, 167.7, 161.0, 140.4, 139.3, 135.9, 133.6, 131.1, 124.9, 123.0, 121.7, 120.8, 119.0, 118.6, 114.3, 110.7, 59.2, 56.2, 53.1, 48.3, 44.5, 38.9, 37.6, 34.8, 33.77, 33.72, 27.92, 27.77, 26.82, 26.5, 23.6, 18.5; minor rotamer: 168.3, 168.0, 161.3, 138.4, 137.5, 135.8, 134.2, 130.0, 125.4, 121.9, 120.0, 119.64, 119.58, 117.9, 113.3, 111.3, 59.6, 56.3, 53.1, 44.6, 42.2, 38.9, 38.3, 37.4, 33.8, 33.6, 28.3, 27.74, 26.79, 26.5, 24.84, 11.9. HRMS (+ESI) calcd for C36H45N5O5S (free base) m/z 660.32142. found m/z 660.32196.

It will be evident to one skilled in the art that the present disclosure is not limited to the foregoing illustrative examples. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A method for preparing the compound

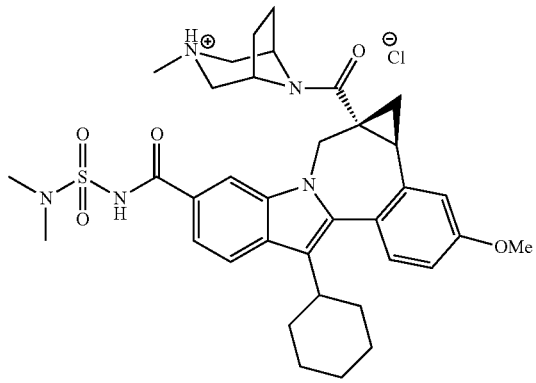

comprising amidation of the compound

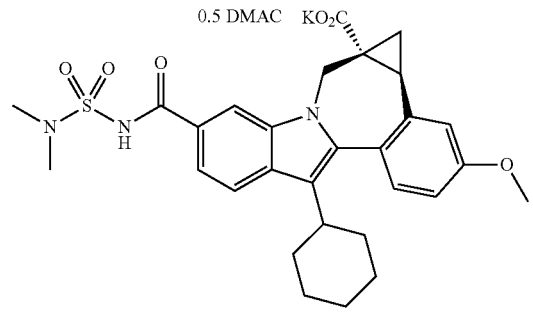

followed by crystallization.

2. The method of claim 1 further comprising the coupling of

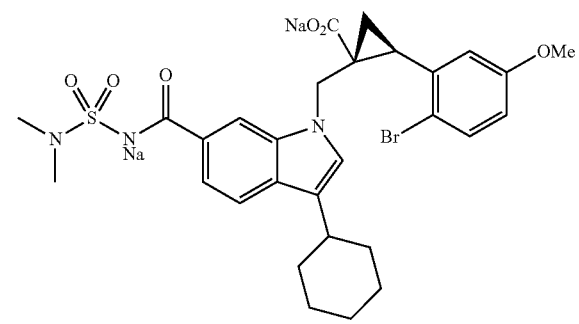

to generate the compound

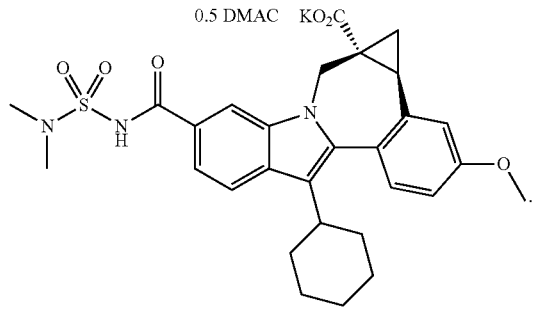

3. The method of claim 2 further comprising the coupling of the compound

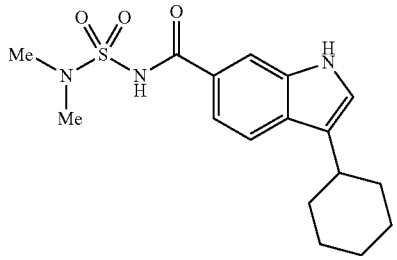 [SMILES: CN(C)S(=O)(=O)NC(=O)c1ccc2c(C3CCCCC3)c[nH]c2c1]

with the compound

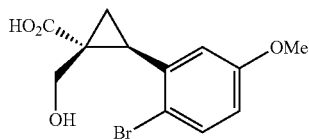 [SMILES: COc1ccc(Br)c([C@@H]2C[C@@]2(CO)C(=O)O)c1]

to generate the compound

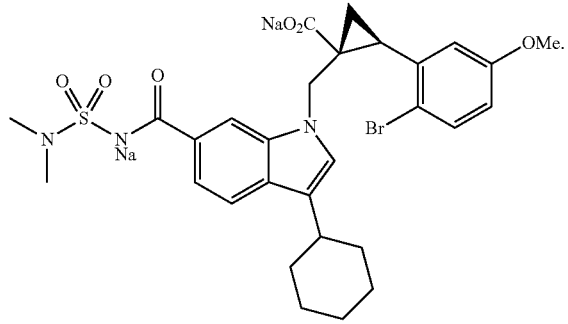

4. The method of claim 3 further comprising the reduction of the compound

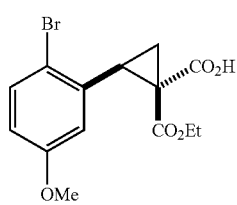

to generate the compound

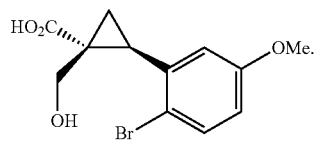 [SMILES: COc1ccc(Br)c([C@@H]2C[C@@]2(CO)C(=O)O)c1]

5. The method of claim 4 further comprising the cyclopropanation and hydrolysis of the compound

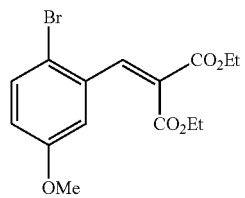

to generate the compound

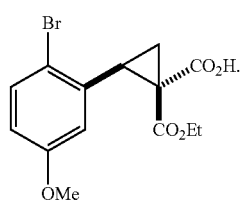

6. A method for the preparation of the compound

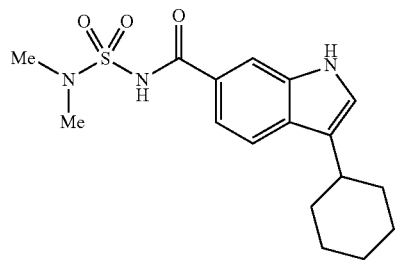 [SMILES: CN(C)S(=O)(=O)NC(=O)c1ccc2c(C3CCCCC3)c[nH]c2c1]

from indole-6-carboxylic acid comprising converting the acid moiety to the dimethylacylsulfonamide moiety followed by coupling to cyclohexanone and reduction.

7. A method for the preparation of the compound

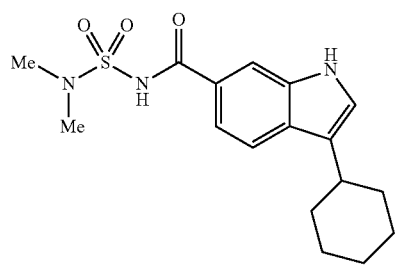 [SMILES: CN(C)S(=O)(=O)NC(=O)c1ccc2c(C3CCCCC3)c[nH]c2c1]

from 6-bromoindole comprising coupling and reduction with cyclohexanone followed by transitional metal catalyzed conversion to the dimethylacylsulfonamide with CO and dimethylsulfamide.
8. The salt compound
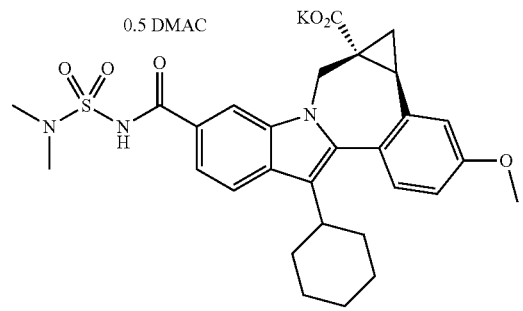
9. The salt compound
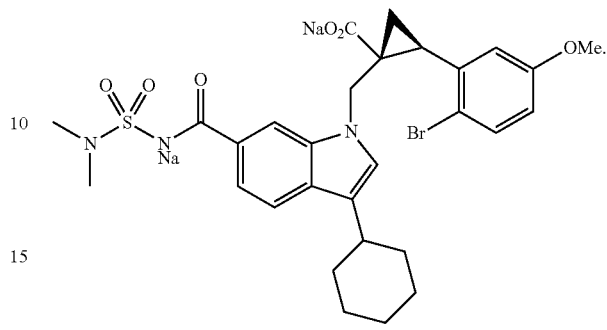
* * * * *